United States Patent [19]

Crivello et al.

[11] 4,399,071

[45] Aug. 16, 1983

[54] METHOD FOR MAKING DIARYLIODONIUM SALTS

[75] Inventors: James V. Crivello, Clifton Park; Julia L. Lee, Schenectady, both of N.Y.

[73] Assignee: General Electric Company, Schenectady, N.Y.

[21] Appl. No.: 357,433

[22] Filed: Mar. 12, 1982

[51] Int. Cl.³ .......................... C07F 9/68; C07F 9/92; C07F 9/00
[52] U.S. Cl. .................................. 260/440; 260/446; 568/6; 568/13; 549/208; 549/212
[58] Field of Search .................. 260/440, 446, 346.22, 260/348.39, 348.41, 348.42; 568/6, 13

[56] References Cited

U.S. PATENT DOCUMENTS 3,981,897  9/1976  Crivello .......................... 260/446 X
4,219,654  8/1980  Crivello ............................ 568/13 X

*Primary Examiner*—Helen M. S. Sneed
*Attorney, Agent, or Firm*—William A. Teoli; James C. Davis, Jr.; James Magee, Jr.

[57] ABSTRACT

A method is provided for making certain diaryliodonium salts which are useful as photoinitiators for a variety of cationic polymerizable organic materials. Reaction is effected between an aromatic iodo compound and an arylorganic aromatic compound in the presence of a peroxy organic acid and an organic sulfonic acid.

8 Claims, No Drawings

METHOD FOR MAKING DIARYLIODONIUM SALTS

CROSS REFERENCE TO RELATED APPLICATIONS

Reference is made to our copending application RD-13859, Alkylaryliodonium Salts and Method for Making, filed concurrently herewith and assigned to the same assignee as the present invention.

BACKGROUND OF THE INVENTION

The present invention relates to a method for making diaryliodonium polyfluoro metal or metalloid salts of the formula, $$[(R)_2 I]^+ MF_d^- \qquad (1)$$

where R is a $C_{(6-13)}$ aryl radical selected from monovalent aromatic hydrocarbon radicals and substituted monovalent aromatic hydrocarbon, M is a metal or metalloid, for example boron, arsenic, antimony and phosphorus, and d is an integer equal to 4-6 inclusive.

Prior to the present invention, the diaryliodonium salts of formula (1) were made by the method shown by Crivello U.S. Pat. No. 3,981,897, which involved the production of an intermediate diaryliodonium bisulfate salt followed by the metathesis of such salt with a polyfluoro compound of the formula, $$XMF_d, \qquad (2)$$

where M and d are as previously defined and X is a positively charged ion of an element selected from hydrogen, alkali metal and alkaline earth metals.

Although the method of Crivello provides a valuable route to a wide variety of diaryliodonium salts of formula (1), the yields of the desired iodonium salt are often unsatisfactory and stringent reaction conditions such as maintaining the temperature of the reaction during the formation of the diaryliodonium bisulfate salt of about 0° C. or below due to the exothermic nature of the reaction renders the process less economically attractive.

Neiland and Karele, Journal of Organic Chemistry, U.S.S.R. 6, 889 (1970) provide an alternate route to the preparation of certain diaryliodonium salts from the reaction of iodosobenzene diacetate and toluene sulfonic acid monohydrate to produce phenyliodoso tosylate and its further condensation with anisole. Koser and Wettach, Journal of Organic Chemistry, 45 1543 (1980) demonstrated that additional diaryliodonium tosylate salts could be made by this general procedure. We have found, however, that these diaryliodonium tosylate salts can be used to initiate thermal and photochemical polymerization of a limited number of cationic polymerizable organic materials, such as certain vinyl ethers. However, these tosylate salts are found to be inactive with other types of cationically polymerizable materials, for example epoxy resins. We have further found facile metathesis of the diaryliodonium tosylate salts of Neilands and Karele, for example 4-methoxydiphenyliodonium tosylate, with the polyfluoro compounds of formula (2) results in diaryliodonium salts within the scope of formula (1) which have been found useful as both thermal and photoinitiators for a wide variety of cationically polymerizable organic materials defined more particularly in U.S. Pat. No. 4,173,551, Crivello, assigned to the same assignee as the present invention.

The present invention is based on the discovery that diaryliodonium salts of formula (1) can be made by effecting reaction between a iodoaryl compound of the formula, $$RI, \qquad (3)$$

where R is as previously defined, and a peracid, and combining the resulting mixture with an organic sulfonic acid and an aryl organic or aromatic compound, defined more particularly below. The ingredients of the resulting mixture are allowed to react to produce a diaryliodonium organic sulfonic acid salt. The diaryliodonium organic sulfonic acid salt is thereafter reacted with a polyfluoro metal compound of formula (2). This procedure results in the production of diaryliodonium salts of formula (1) at significantly improved yields over the prior art, while avoiding the stringent reaction conditions often found necessary such as the low temperature requirements and long reaction times of the diaryliodonium bisulfate method.

STATEMENT OF THE INVENTION

There is provided by the present invention, a method for making a diaryliodonium salt of formula (1), which comprises (1) incrementally adding a peracid to an iodoaryl compound of formula (3), to provide a mixture of from about 1 to 3 moles of peracid, per mole of iodoaryl compound, (2) combining the mixture of (1) with a mixture of a $C_{(1-13)}$ organic sulfonic acid and a $C_{(6-13)}$ aryl organic compound selected from a substituted and unsubstituted aromatic hydrocarbon, or $C_{(5-13)}$ heteroaromtic compound to produce a mixture having about one mole of the $C_{(1-13)}$ organic sulfonic acid, and about one mole of the aryl organic compound, per mole of the iodoaryl compound, (3) allowing the ingredients of (2) to react to produce a diaryliodonium organosulfonic acid salt, (4) recovering the diaryliodonium organic sulfonic acid salt from (3), (5) effecting a metathesis between the diaryliodonium organic acid salt of (4) and a polyfluoro metal or metalloid salt of formula (2), (6) recovering the resulting diaryliodonium polyfluoro metalloid salt from the mixture of (5), and (7) washing the recovered diaryliodonium polyfluoro metalloid salt of (6) to effect removal therefrom of the by-product organic sulfonic acid metal salt.

Radicals included within R of formula (1) can be the same or different $C_{(6-13)}$ aromtic carbocyclic or $C_{(5-13)}$ heterocyclic radicals which can be substituted with from 1-5 monovalent radicals selected from $C_{(1-8)}$ alkoxy, $C_{(1-8)}$ alkyl, nitro, chloro, etc. R is more particularly phenyl, chlorophenyl, nitrophenyl, methoxyphenyl, pyridyl, etc.

Included within the diaryliodonium salts shown by formula (1) are, for example,

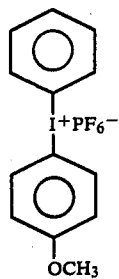
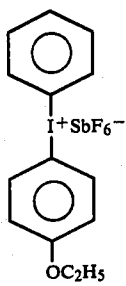
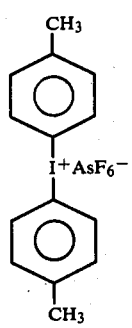
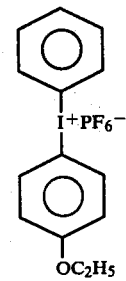
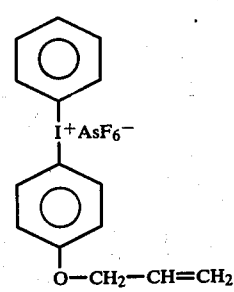
-continued
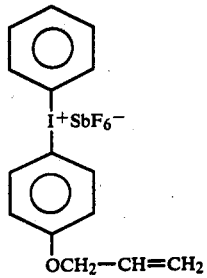
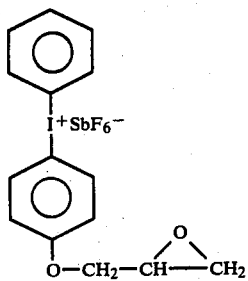
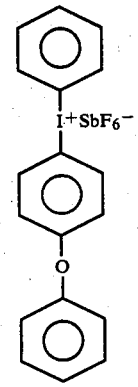
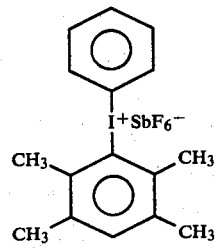
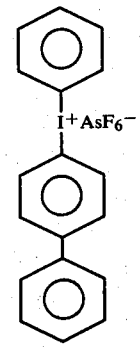

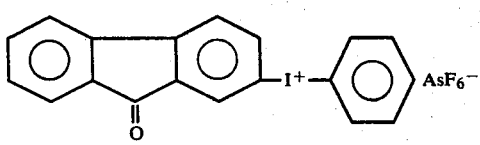

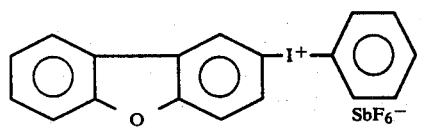

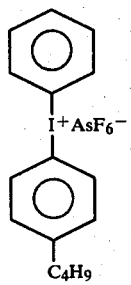

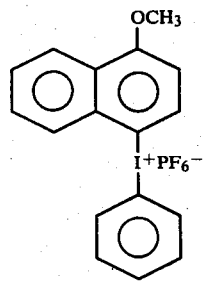

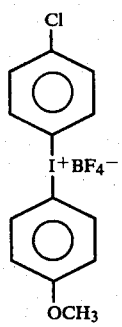

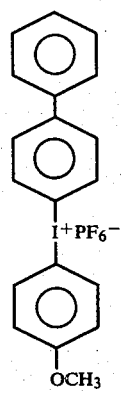

Some of the polyfluoro compounds shown by formula (2), are for example, NaSbF$_6$, NaAsF$_6$, KAsF$_6$, KPF$_6$, NaBF$_4$, Ca(PF$_6$)$_2$, Mg(AsF$_6$)$_2$, Ba(BF$_4$)$_2$, HPF$_6$, HAsF$_6$, HBF$_4$, HSbF$_6$, Among the iodo aryl compounds of formula (3) there can be included

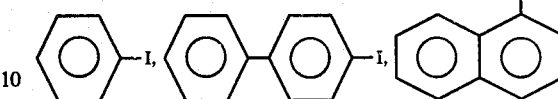

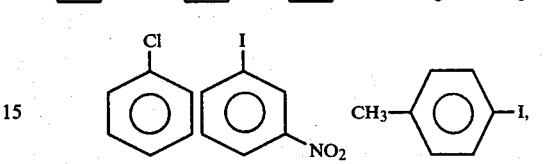

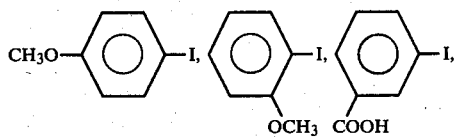

Typical of the cationically polymerizable organic materials which can be cured with the diaryliodonium salts of formula (1), are for example, any monomeric, dimeric or oligomeric or polymeric epoxy material containing one or a plurality of epoxy functional groups. For example, those resins which result from the reaction of bisphenol-A (4,4'-isopropylidenediphenol) and epichlorohydrin, or by the reaction of low molecular weight phenol-formaldehyde resin (Novolak resin) with epichlorohydrin, can be used alone or in combination with an epoxy containing compound as a reactive diluent. Such diluents as phenyl glycidyl ether, 4-vinyl-cyclohexene dioxide, limonene dioxide, 1,2-cyclohexene oxide, glycidyl acrylate, glycidyl methacrylate, styrene oxide, allyl glycidyl ether, etc., may be added as viscosity modifying agents.

In addition, the range of these compounds can be extended to include polymeric materials containing terminal or pendant epoxy groups. Examples of these compounds are vinyl copolymers containing glycidyl acrylate or methacrylate as one of the comonomers. Other classes of epoxy containing polymers amenable to cure using the above catalysts are epoxy siloxane resins, epoxy-polyurethanes and epoxy-polyesters. Such polymers usually have epoxy functional groups at the ends of their chains. Epoxy-siloxane resins and method for making are more particularly shown by E. P. Pluedemann and G. Fanger, J. Am. Chem. Soc., 80, 632-5, (1959). As described in the literature, epoxy resins can also be modified in a number of standard ways such as reaction with amines, carboxylic acids, thiols, phenols, alcohols, etc., as shown in U.S. Pat. Nos. 2,935,488; 3,235,620; 3,369,055; 3,379,653; 3,398,211; 3,403,199; 3,563,840; 3,567,797; 3,677,995; etc. Further coreactants which can be used with epoxy resins are hydroxy terminated flexibilizers such as hydroxy terminated polyesters, shown in the Encyclopedia of Polymer Science and Technology, Vol. 6, 1967, Interscience Publishers, New York, pp. 209-271 and particularly p. 238.

Included by the thermosetting organic condensation resins of formaldehyde which can be used in the practice of the present invention are, for example, urea type resins, phenol-formaldehyde type resins.

In addition, there can be used melamine-thiourea resins, melamine, or urea-aldehyde resins, cresol-formaldehyde resins and combinations with other carboxy, hydroxyl, amino and mercapto containing resins, such as polyester, alkyds and polysulfides.

Some of the vinyl organic prepolymers which can be used to make the polymerizable compositions of the present invention are, for example $CH_2=CH-O-(CH_2-CH_2O)_{n'}-CH=CH_2$, where n' is a positive integer having a value up to about 1000 or higher, multifunctional vinylethers, such as 1,2,3-propane trivinylether, trimethylolpropane, trivinylether, prepolymers having the formula,

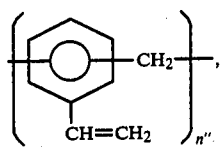

low molecular weight polybutadiene having a viscosity of from 200 to 10,000 centipoises at 25° C., etc. Products resulting from the cure of such compositions can be used as printing inks and other applications typical of thermosetting resins.

A further category of the organic materials which can be used to make the polymerizable compositions are cyclic ethers which are convertible to thermoplastics. Included by such cyclic ethers, are, for example, oxetanes such as 3,3-bischloromethyloxetane, alkoxyoxetanes as shown by Schroeter U.S. Pat. No. 3,673,216, assigned to the same assignee as the present invention; oxolanes such as tetrahydrofuran, oxepanes, oxygen containing spiro compounds, trioxane, dioxolane, etc.

In addition to cyclic ethers there are also included cyclic esters such as beta-lactones, for example propiolactone, pivalolactone, cyclic amines, such as 1,3,3-trimethyl-azetidine and organosilicon cyclics, for example, materials included by the formula,

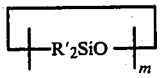

where R' can be the same or different monovalent organic radical such as methyl or phenyl and m is an integer equal to 3 to 8 inclusive. An example of an organosilicon cyclic is hexamethyl trisiloxane, octamethyl tetrasiloxane, etc. The products made in accordance with the present invention are high molecular weight oils and gums.

In the practice of the invention, initial reaction is effected between the iodo aryl compound and the peracid to produce an aryliodosoacylate. Preferably, the peracid, which can include for example, peracetic acid, peroxybutyric acid, perbenzoic acid, peroxypropionic acid, m-chloroperbenzoic acid, etc., can be added dropwise or incrementally to the iodoaryl compound while the temperature is maintained below about 40° C. Effective results can be achieved with the use of about 1 to 3 moles of peracid per mole of the iodoaryl compound.

After the addition of the peracid is completed there can be added to the mixture a strong alkyl or arylsulfonic acid, for example, benzene sulfonic acid, 3-nitrobenzene sulfonic acid, 3-chlorobenzene sulfonic acid, trifluoromethane sulfonic acid, methane sulfonic acid, p-toluene sulfonic acid, etc., along with an aromatic substrate, for example anisole, allylphenylether, diphenylether, benzene, toluene, xylene, etc. It is preferred to use p-toluene sulfonic acid as the organic sulfonic acid and an aromatic substrate which is activated by electron releasing substituents. There can be used from 1 to 3 moles of the organic sulfonic acid and 1 to 3 moles of the aromatic substrate per mole of the iodoaryl compound initially utilized. The resulting mixture can be agitated from 0.25 to 25 hours at a temperature in the range of from 0° C. to 100° C. and preferably from 25° C. to 100° C. The resulting diaryliodonium organic sufonic acid salt can be isolated from the reaction mixture by trituration based on the addition of solvent such as diethyl ether, followed by the filtration of the resulting crystals. These crystals can thereafter be washed with an appropriate organic solvent, for example diethyl ether.

The metathesis of the diaryliodonium organic sulfonate with the polyfluoro compound can thereafter be achieved with addition of the polyfluoro compound to water or a suitable organic solvent. Suitable inert organic solvents, are for example, methyl ethyl ketone, acetone, ethanol, methanol, 1,1,1-trichloroethane, acetonitrile, nitromethane, etc. There can be utilized from 1 to 3 mole of the polyfluoro compound per mole of the diaryliodonium organic sulfonic acid salt. Recovery of the diaryliodonium polyfluoro metal or metalloid salt can be achieved by filtering the resulting alkali metal or alkaline earth metal organic sulfonic acid salt from the reaction mixture, followed by the evaporation of the organic solvent from the resulting filtrate.

In order that those skilled in the art will be better able to practice the invention, the following examples are given by way of illustration and not by way of limitation.

EXAMPLE 1

There was added dropwise, 45.6 grams (0.24 mole) of 40% peracetic acid to 20.4 grams (0.1 mole) of iodobenzene while the temperature was maintained at less than 30° C. After the addition of the peracid, there was added to the resulting mixture 19.05 grams (0.1 mole) of p-toluene sulfonic acid monohydrate, 10.8 grams (0.1 mole) of anisole and 10 ml of glacial acetic acid. The resulting mixture was stirred for 2 hours. The 4-methoxyphenyliodonium tosylate was isolated from the reaction mixture by trituration with diethyl ether, filtering and further washing with diethyl ether. There was obtained 41.8 grams or an 86.7% yield of a product having a melting point of 163°-165° C. Based on method of preparation, the product was 4-methoxyphenyliodonium tosylate.

There was added 22.5 grams (0.087 mole) of sodium hexafluoroantimonate to a solution of 41.8 grams (0.087 mole) of 4-methoxydiphenyliodonium tosylate dissolved in 200 ml of methyl ethyl ketone. The resulting reaction mixture was heated to 50°-60° C. with stirring for 1 hour. The sodium tosylate by-product precipitated from the solution. The reaction mixture was suction filtered and the solid sodium tosylate was washed with fresh methyl ethyl ketone. The filtrate was then stripped of solvent on rotary evaporator leaving a pale yellow orange oil. The product crystallized after being washed with a small amount of diethyl ether. The product was obtained by suction filtration. There was obtained 42.94 grams or a 90.3% yield of product having an MP of 95°-97° C. Based on method of preparation, the product was 4-methoxydiphenyliodonium hexafluoroantimonate.

When 1% of the above iodonium salt was dissolved in 4-vinylcyclohexene dioxide and applied onto a glass substrate, irradiated under a GE H3T7 medium pressure mercury arc lamp, at a distance of 4 inches, a tack-free hard coating was obtained within 1-2 seconds.

EXAMPLE 2

There was added 456 grams (2.4 mole) of 40% peracetic acid to 204 grams (1.0 mole) of iodobenzene. Upon completion of the addition of the peracid, 190.2 grams (1.0 mole) of p-toluene sulfonic acid monohydrate was added to the mixture and the resulting reaction mixture was stirred for 1 hour. A product crystallized from solution which was isolated by suction filtration and washed with methylene chloride. There was obtained 226.5 grams, or an 83.3% yield of product having a melting point of 140°-142° C. Based on method of preparation, the product was phenyliodoso tosylate.

A mixture of 5 grams of allylphenylether, 20 ml of glacial acetic acid and 7.84 grams of phenyliodoso tosylate was stirred. After stirring at 25° C. for 90 minutes, diethyl ether was added to the mixture. A product crystallized from the mixture which was filtered and washed with diethyle ether. There was obtained 9.4 grams or a 94.8% yield of product having a melting point of 90°-95° C. Based on method of preparation, the product was 4-allyloxydiphenyliodonium tosylate.

There was added 5 grams of sodium hexafluoroantimonate to a solution of 9.4 grams of the 4-allyloxydiphenyliodonium tosylate dissolved in 70 ml of methyl ethyl ketone. After 1 hour, the solution was filtered to remove sodium tosylate and the solvent in the resulting filtrate was removed under vacuo. There was obtained an oil which crystallized slowly on standing. An 85.5% yield of product (9.8 grams) was obtained. Based on method of preparation the product was 4-allyloxydiphenyliodonium hexafluoroantimonate.

A 1% solution of the above diphenyliodonium salt in limonene dioxide was found to cure within 2 seconds exposed as a film on a glass slide under a GE H3T7 medium pressure mercury arc lamp at a distance of 4 inches.

EXAMPLE 3

A mixture of 9.3 grams (0.023 mole) phenyliodoso tosylate and 9.25 grams (0.06 mole) biphenyl was heated to 135° C. for 1 hour and the mixture poured into 50 ml diethyl ether. After filtering off the insoluble salt and washing with ether, the product was dried. A 63% yield of biphenylyl phenyl iodonium tosylate was obtained.

The above salt was suspended in 50 ml water and 4.0 grams $KAsF_6$ was added. After stirring for 1 hour, the insoluble biphenylyl phenyl iodonium hexafluoroarsenate was isolated by suction filtration, washed with water and dried to give a 905 yield, based on the starting tosylate salt.

A 0.5% solution of the above salt in 4-vinylcyclohexene dioxide cured in 10 seconds when irradiated as described in Example 1.

EXAMPLE 4

A mixture of 1.70 gram phenyl ether, 3.92 grams phenyliodoso tosylate and 20 ml glacial acetic acid was allowed to stir at room temperature for 1 hour and then 50 ml diethyl ether was added. A product precipitated which was washed with fresh diethyl ether and dried. Based on method of preparation there was obtained 3.9 grams or a 74% yield of 4-phenoxydiphenyliodonium tosylate. Elemental analysis Calc. for $C_{20}H_{19}IO_4S$: %C, 49.80; %H, 3.94; %I, 26.35; %S, 6.65. Found: %C, 50.03; %H, 3.97; %I, 26.54; %S, 6.66.

The above product was suspended in 50 ml water and 1.50 grams (0.7 mole) $KAsF_6$ was added. The product obtained after 1 hour at room temperature was an oil which by method of preparation was 4-phenoxydiphenyl iodonium hexafluoroarsenate. A 1% solution of the above iodonium salt dissolved in 4-vinylcyclohexene dioxide gave a 3 second tack-free UV cure time when exposed to ultraviolet light as described in Example 2.

EXAMPLE 5

There was added dropwise, 45.6 grams (0.24 mole) of 40% peracetic acid to 21.8 grams (0.1 mole) of p-iodotoluene in 10 ml of methylene chloride and 10 ml glacial acetic acid. When the addition was complete, 19.05 grams (0.1 mole) p-toluenesulfonic acid monohydrate and 10.8 grams (0.1 mole) anisole were added and the reaction mixture cooled in an ice bath. After 2.5 hours, 50 ml diethyl ether was added to the mixture. A product precipitated which was filtered and dried. There was obtained 45.2 grams (91%) of product. Based on method of preparation, the product was 4-methyl-4'-methoxydiphenyliodonium tosylate.

The above tosylate salt was dissolved in 100 ml acetone and 25.9 grams $NaSbF_6$ dissolved in 164 ml acetone were added. The solution was filtered to remove sodium tosylate and the acetone removed by means of a flash evaporator to give 40 grams (71% yield) of 4-methyl-4'-methoxydiphenyliodonium hexafluoroantimonate as an oil. A 1% solution of the iodonium salt in 4-vinylcyclohexene dioxide gave a UV cure tack-free time of 3 seconds when exposed to ultraviolet light as described in Example 1.

EXAMPLE 6

A mixture of 16.8 grams (0.1 mole) dibenzofuran and 39.2 grams (0.1 mole) phenyliodoso tosylate in 150 ml glacial acetic acid was stirred for 3.5 hours at 50° C. There was added to the mixture, 200 ml diethyl ether which resulted in the precipitation of 3-dibenzofuranyl phenyl iodonium tosylate. The mixture was suspended in water to remove unreacted phenyliodoso tosylate then filtered and dried. A 62.5% yield of the above salt was obtained having a melting point of 188°-190° C.

There was added 19.35 grams (0.075 mole) of $NaSbF_6$ to 40.5 grams (0.075 mole) of the above tosylate salt dissolved in 150 ml methyl ethyl ketone. The reaction mixture was warmed to 40° C. and held at that temperature for one hour. The solution was filtered to remove sodium tosylate and the solvent removed by means of a flash evaporator. An oil remained which solidified when washed with ether. There was obtained a 78% yield of product having a melting point of 180°-190° C. The product was phenyl-3-dibenzofuranyl iodonium hexafluoroantimonate.

A tack-free UV cure time of 1-2 seconds was recorded when 4-vinylcyclohexene dioxide was sensitized with 1% of the above described iodonium hexafluoroantimonate and UV cured as described in Example 2.

Although the above examples are directed to only a few of the very many variables which can be present in the practice of the present invention, it should be understood that practice of the present invention is directed to the use of a much broader variety of iodo aryl compounds, peracids, organic sulfonic acids and polyfluoro metalloid salts which are shown in the description preceding these examples.

What we claim as new and desire to secure by Letters Patent of the United States is:

1. A method for making a diaryliodonium salt which comprises,
    (1) incrementally adding a peracid to a $C_{(1-13)}$ iodo aryl compound to provide a mixture of from about 1-3 moles of peracid per mole of iodo aryl compound,
    (2) combining the mixture of (1) with a mixture of a $C_{(1-13)}$ organic sulfonic acid and a $C_{(6-13)}$ aryl organic compound selected from a substituted and unsubstituted aromatic hydrocarbon to produce a mixture having about 1 mole of the $C_{(1-13)}$ organic sulfonic acid and about 1 mole of the aryl organic compound per mole of the iodo aryl compound,
    (3) allowing the ingredients of (2) to react to produce a diaryliodonium organosulfonic acid salt,
    (4) recovering the diaryliodonium organic sulfonic acid salt from (3),
    (5) effecting a metathesis between the diaryliodonium organic acid salt of (4) and a polyfluoro metal or metalloid salt of the formula, $$XMF_d,$$

(6) recovering the resulting diaryliodonium polyfluoro metalloid salt from the mixture of (5), and
    (7) washing the recovered diaryliodonium polyfluoro metalloid salt of (6) to effect removal therefrom of the by-product organic sulfonic acid metal salt, where M is a metal or metalloid, X is an ion of an element selected from hydrogen, alkali metals and alkaline earth metals, and d is an integer equal to 4-6 inclusive.

2. A method for making 4-methoxydiphenyliodonium hexafluoroantimonate which comprises
    (1) incrementally adding peracetic acid to iodobenzene at a temperature of below about 40° C. to provide a mixture having from about 1 to 3 moles of peracetic acid per mole of iodobenzene,
    (2) combining the mixture of (1) with p-toluene sulfonic acid monohydrate and anisole to produce a mixture having about 1 mole of the p-toluene sulfonic acid monohydrate and anisole, per mole of the iodobenzene,
    (3) allowing the ingredients of the mixture of (2) to react to produce 4-methoxyphenyliodonium tosylate,
    (4) recovering the 4-methoxyphenyliodonium tosylate of (3),
    (5) effecting methathesis between the 4-methoxyphenyliodonium tosylate and sodium hexafluoroantimonate,
    (6) recovering the 4-methoxydiphenyliodonium hexafluoroantimonate from the mixture of (5) and
    (7) washing the 4-methoxydiphenyliodonium hexafluoroantimonate to effect the removal therefrom of sodium p-toluene sulfonic acid monohydrate.

3. A method in accordance with claim 1, where the iodo aryl compound is iodobenzene.

4. A method in accordance with claim 1, where the aryl organic compound of (2) is allyl phenyl ether.

5. A method in accordance with claim 1, where the aryl organic compound of (2) is biphenyl.

6. A method in accordance with claim 1, where the aryl organic compound of (2) is phenylether.

7. A method in accordance with claim 1, where the iodo aryl compound is iodoaryl toluene.

8. A method in accordance with claim 1, where the aryl organic compound is dibenzofuran.

* * * * *

UNITED STATES PATENT AND TRADEMARK OFFICE
CERTIFICATE OF CORRECTION

PATENT NO. : 4,399,071

DATED : August 16, 1983

INVENTOR(S) : Crivello et al.

It is certified that error appears in the above-identified patent and that said Letters Patent is hereby corrected as shown below:

Column 11, line 12, cancel "a $C_{(1-13)}$" and substitute -an-

Signed and Sealed this

Twenty-ninth Day of November 1983

[SEAL]

Attest:

GERALD J. MOSSINGHOFF

Attesting Officer — Commissioner of Patents and Trademarks